United States Patent
Prema Mohanasundaram et al.

(10) Patent No.: US 11,241,236 B2
(45) Date of Patent: Feb. 8, 2022

(54) BUTTRESS ATTACHMENT METHODS FOR CIRCULAR EEA STAPLERS

(71) Applicant: Covidien LP, Mansfield, MA (US)

(72) Inventors: Suresh Kumar Prema Mohanasundaram, Chennai (IN); Sumit Bali, Hyderabad (IN)

(73) Assignee: Covidien LP, Mansfield, MA (US)

(*) Notice: Subject to any disclaimer, the term of this patent is extended or adjusted under 35 U.S.C. 154(b) by 103 days.

(21) Appl. No.: 16/540,422

(22) Filed: Aug. 14, 2019

(65) Prior Publication Data

US 2020/0093494 A1   Mar. 26, 2020

Related U.S. Application Data (60) Provisional application No. 62/734,297, filed on Sep. 21, 2018.

(51) Int. Cl.
| | |
|---|---|
| *A61B 17/068* | (2006.01) |
| *A61B 17/115* | (2006.01) |
| *A61B 17/072* | (2006.01) |

(52) U.S. Cl.
CPC .... *A61B 17/1155* (2013.01); *A61B 17/07292* (2013.01); *A61B 2017/07221* (2013.01);
(Continued)

(58) Field of Classification Search
CPC ............................................... A61B 17/07292
See application file for complete search history.

(56) References Cited

U.S. PATENT DOCUMENTS

| | | |
|---|---|---|
| 4,473,077 A | 9/1984 | Noiles et al. |
| 4,576,167 A | 3/1986 | Noiles |
| (Continued) | | |

FOREIGN PATENT DOCUMENTS

| | | |
|---|---|---|
| EP | 2620106 A2 | 7/2013 |
| EP | 2742872 A1 | 6/2014 |
| (Continued) | | |

OTHER PUBLICATIONS

Extended European Search Report issued in EP Application No. 19198757.7, dated Jun. 25, 2020.
(Continued)

*Primary Examiner* — Eyamindae C Jallow
(74) *Attorney, Agent, or Firm* — Carter, DeLuca & Farrell LLP (57) ABSTRACT

An apparatus for joining two hollow organ sections includes a staple cartridge assembly including an annular wall, an anvil assembly, a buttress member, and a fastening member. The annular wall of the staple cartridge assembly defines an inner aperture in an inner surface thereof and an outer aperture in an outer surface thereof. The buttress member is configured to be positioned on a distal surface of the staple cartridge assembly. The buttress member defines a cutout on a peripheral portion thereof. The fastening member has a first end securely affixed to the inner aperture of the annular wall of the staple cartridge assembly and a second end securely affixed to the outer aperture of the annular wall of the staple cartridge assembly to secure the buttress member on the staple cartridge assembly. The cutout of the buttress member is in registration with the outer aperture of the annular wall.

17 Claims, 7 Drawing Sheets

(52) U.S. Cl.
CPC .............. *A61B 2017/07257* (2013.01); *A61B 2017/07271* (2013.01)

(56) References Cited

U.S. PATENT DOCUMENTS

| | | | |
|---|---|---|---|
| 4,646,745 | A | 3/1987 | Noiles |
| 5,005,749 | A | 4/1991 | Aranyi |
| 5,119,983 | A | 6/1992 | Green et al. |
| 5,588,579 | A | 12/1996 | Schnut et al. |
| 6,053,390 | A | 4/2000 | Green et al. |
| 8,028,883 | B2* | 10/2011 | Stopek ................. A61B 17/068 227/175.1 |
| 9,010,609 | B2* | 4/2015 | Carter ................. A61B 17/1155 227/176.1 |
| 9,345,479 | B2* | 5/2016 | (Tarinelli) Racenet ....................... A61B 17/07207 |
| 10,420,556 | B2* | 9/2019 | Kostrzewski .......... A61B 17/32 |
| 2005/0059996 | A1* | 3/2005 | Bauman ............... A61B 17/115 606/215 |
| 2005/0059997 | A1* | 3/2005 | Bauman ............... A61B 17/115 606/219 |
| 2009/0001122 | A1 | 1/2009 | Prommersberger et al. |
| 2011/0087279 | A1* | 4/2011 | Shah ................ A61B 17/07207 606/219 |
| 2013/0153638 | A1* | 6/2013 | Carter ................. A61B 17/1155 227/179.1 |
| 2013/0193191 | A1* | 8/2013 | Stevenson ........ A61B 17/07292 227/179.1 |
| 2014/0097224 | A1 | 4/2014 | Prior |
| 2014/0217148 | A1* | 8/2014 | Penna ................. A61B 17/0682 227/179.1 |
| 2014/0224686 | A1* | 8/2014 | Aronhalt .......... A61B 17/07292 206/339 |
| 2015/0122872 | A1* | 5/2015 | Olson .............. A61B 17/07292 227/179.1 |
| 2015/0327864 | A1 | 11/2015 | Hodgkinson et al. |
| 2017/0281182 | A1* | 10/2017 | Nativ ................... A61B 17/072 |
| 2018/0360460 | A1 | 12/2018 | Mozdzierz et al. |
| 2019/0038285 | A1* | 2/2019 | Mozdzierz ....... A61B 17/07207 |
| 2019/0175172 | A1* | 6/2019 | Kollar .............. A61B 17/07292 |
| 2019/0269409 | A1* | 9/2019 | Prior ................. A61B 17/1155 |

FOREIGN PATENT DOCUMENTS

| | | |
|---|---|---|
| EP | 2754399 A2 | 7/2014 |
| EP | 2774551 A2 | 9/2014 |

OTHER PUBLICATIONS

Partial European Search Report issued in European Patent Application No. 19198757.7, dated Feb. 7, 2020.

* cited by examiner

BUTTRESS ATTACHMENT METHODS FOR CIRCULAR EEA STAPLERS

CROSS-REFERENCE TO RELATED APPLICATIONS

This application claims the benefit of and priority to U.S. Provisional Patent Application Ser. No. 62/734,297 filed Sep. 21, 2018, the entire disclosure of which is incorporated by reference herein.

BACKGROUND

Technical Field

The present disclosure relates to a surgical apparatus for applying surgical fasteners or staples to body tissue, and more particularly, to a surgical buttress for use with an end-to-end anastomosis stapling apparatus.

Background of Related Art

Anastomosis is a surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by either circular, end-to-end or side-to-side organ reconstruction methods.

In a circular anastomosis procedure, the two ends of the organ sections are joined by means of a stapling apparatus, which drives a circular array of staples through the end section of each organ section and simultaneously cores any tissue interior of the driven circular array of staples to free the tubular passage. Typically, these apparatuses include an elongated shaft having a handle portion at a proximal end to actuate the apparatus and a staple holding component disposed at a distal end. An anvil assembly including an anvil shaft with attached anvil head is mounted to the distal end adjacent the staple holding component. Opposed end sections of the organ to be stapled are clamped between the anvil head and the staple holding component. The clamped tissue is stapled by driving a plurality of staples from the staple holding component so that the ends of the staples pass through the tissue and are deformed by the anvil head.

In use, one end section of the organ is secured about the anvil assembly and the other end section of the organ is held in place adjacent the staple holding component. The shaft of the anvil assembly is removably connected to the apparatus. Once the anvil shaft is secured to the apparatus, the anvil is drawn into close approximation to the staple holding component. The apparatus is then fired to cause the staples to pass through tissue of both sections of the organ and deform against the anvil. During the firing step, a circular knife is advanced to cut tissue inside the staple line, thereby establishing a passage between the two sections of the organ. After firing, the apparatus is typically removed by withdrawing the anvil through the staple line, after which the surgeon will carefully inspect the surgical site to ensure a proper anastomosis has been achieved.

In certain surgical procedures, buttress or reinforcing materials have been utilized in connection with circular stapling apparatuses. However, due to the inherent difficulty in positioning and securing such materials with the apparatus, a need exists for the buttress material that can be safely and effectively positioned within staple cartridge and/or anvil assemblies.

SUMMARY

In accordance with an embodiment of the present disclosure, an apparatus for joining two hollow organ sections with an annular array of surgical staples includes a staple cartridge assembly, an anvil assembly, a buttress member, and a fastening member. The staple cartridge assembly includes an annular wall having the annular array of surgical staples. In particular, the annular wall defines an inner aperture in an inner surface of the annular wall and an outer aperture in an outer surface of the annular wall. The anvil assembly is movable relative to the staple cartridge assembly between spaced apart and approximated positions to adjustably clamp the two hollow organ sections between the staple cartridge and anvil assemblies. The buttress member is configured to be positioned on a distal surface of the staple cartridge assembly. The buttress member defines a cutout on a peripheral portion thereof. The fastening member has a first end securely affixed to the inner aperture of the annular wall of the staple cartridge assembly and a second end securely affixed to the outer aperture of the annular wall of the staple cartridge assembly to secure the buttress member on the staple cartridge assembly. The cutout of the buttress member is in radial registration with the outer aperture of the annular wall.

In an embodiment, the cutout of the buttress member may be dimensioned to receive the fastening member therethrough.

In another embodiment, at least one of the first end or the second end of the fastening member may be securely affixed to the respective inner or outer apertures by an adhesive.

In yet another embodiment, the inner aperture and the outer aperture may be in communication with each other to define a bore therebetween.

In still yet another embodiment, the fastening member may be dimensioned to be received through the bore of the annular wall of the staple cartridge assembly such that the first and second ends extending through the first and second apertures are tied to secure the buttress member on the staple cartridge assembly.

In yet another embodiment, the buttress member may have an annular configuration. The buttress member may be concentrically disposed in a juxtaposed relation with the annular array of surgical staples.

In still another embodiment, the buttress member may further define a plurality of cutouts circumferentially arranged around the peripheral portion of the buttress member.

In an embodiment, the staple cartridge assembly may further include a cylindrical knife disposed radially inward of the buttress member.

In another embodiment, the fastening member secured to the inner and outer apertures of the annular wall of the staple cartridge assembly may be looped around the cylindrical knife such that the fastening member is severed by the cylindrical knife when the cylindrical knife is axially displaced.

In an embodiment, the fastening member may be a suture.

In accordance with another embodiment of the present disclosure, an apparatus for joining two hollow organ sections with an annular array of surgical staples includes a staple cartridge assembly, an anvil assembly, and a buttress assembly. The staple cartridge assembly includes an annular array of surgical staples. The anvil assembly is movable relative to the staple cartridge assembly between spaced apart and approximated positions to adjustably clamp the two hollow organ sections between the staple cartridge and anvil assemblies. The anvil assembly includes an anvil member and a shaft extending from the anvil member. The anvil member includes a proximal surface defining a first aperture and a peripheral portion defining a second aperture. The buttress assembly includes a buttress member and a fastening member. The buttress member is dimensioned to be positioned on the proximal surface of the anvil assembly. The buttress member is secured to the anvil assembly by the fastening member having a first end affixed to the first aperture and a second end affixed to the second aperture. The buttress member defines a cutout dimensioned to receive the fastening member therethrough.

In an embodiment, the cutout of the buttress member may be in registration with the second aperture of the anvil member.

In another embodiment, an outer peripheral portion of the proximal surface of the anvil member may include a stepped portion configured to receive the buttress member such that the buttress member is flush with an inner member of the proximal surface of the anvil member. The inner member may be radially inward of the outer peripheral portion of the proximal surface.

In accordance with yet another embodiment of the present disclosure, a buttress member includes an inner portion and a peripheral portion. The inner portion has flaps circumferentially arranged about the center of the inner portion. The inner portion defines cutouts. Each cutout is interposed between a pair of flaps. The flaps are coterminous at the center of the inner portion. The flaps are formed of resilient material such that when a shaft of an anvil assembly or an approximation shaft of a staple cartridge assembly of the apparatus is inserted therethrough, the flaps jointly secure the buttress member to the shaft of the anvil assembly or the approximation shaft of the staple cartridge assembly. The peripheral portion is disposed radially outward of the inner portion. The inner portion and the outer portion are integrally formed as a single construct.

The inner portion is severable from the peripheral portion.

In an embodiment, the flaps may be tapered towards the center of the inner portion.

In another embodiment, the cutouts may define a diameter smaller than a diameter of the shaft of the anvil assembly or a diameter of the approximation shaft of the staple cartridge assembly.

In accordance with yet another embodiment of the present disclosure, a buttress member includes an annular body dimensioned to be secured to an anvil assembly or a staple cartridge assembly of the apparatus by an adhesive. The annular body includes a peripheral portion defining a plurality of circumferentially arranged perforations configured for deposit of the adhesive therein. The annular body is dimensioned to be disposed radially outward of a cylindrical knife concentrically arranged in the staple cartridge assembly.

BRIEF DESCRIPTION OF THE DRAWINGS

Various embodiments of the present disclosure are described hereinbelow with reference to the drawings, wherein:

FIG. 4 is a perspective view of a buttress member of the surgical buttress assembly of

FIG. 2;

FIG. 9 is a side view of the staple cartridge assembly of FIG. 1 in conjunction with a buttress member in accordance with another embodiment of the present disclosure;

FIG. 10 is a side view of the anvil assembly of FIG. 1 and the buttress member of

FIG. 9;

DETAILED DESCRIPTION OF EMBODIMENTS

Embodiments of the present disclosure will now be described in detail with reference to the drawings, in which like reference numerals designate identical or corresponding elements in each of the several views. As used herein, the term "distal," as is conventional, will refer to that portion of the apparatus, apparatus, device or component thereof which is farther from the user while, the term "proximal," will refer to that portion of the apparatus, apparatus, device or component thereof which is closer to the user. In the following description, well-known functions or constructions are not described in detail to avoid obscuring the present disclosure in unnecessary detail.

Figure 1:
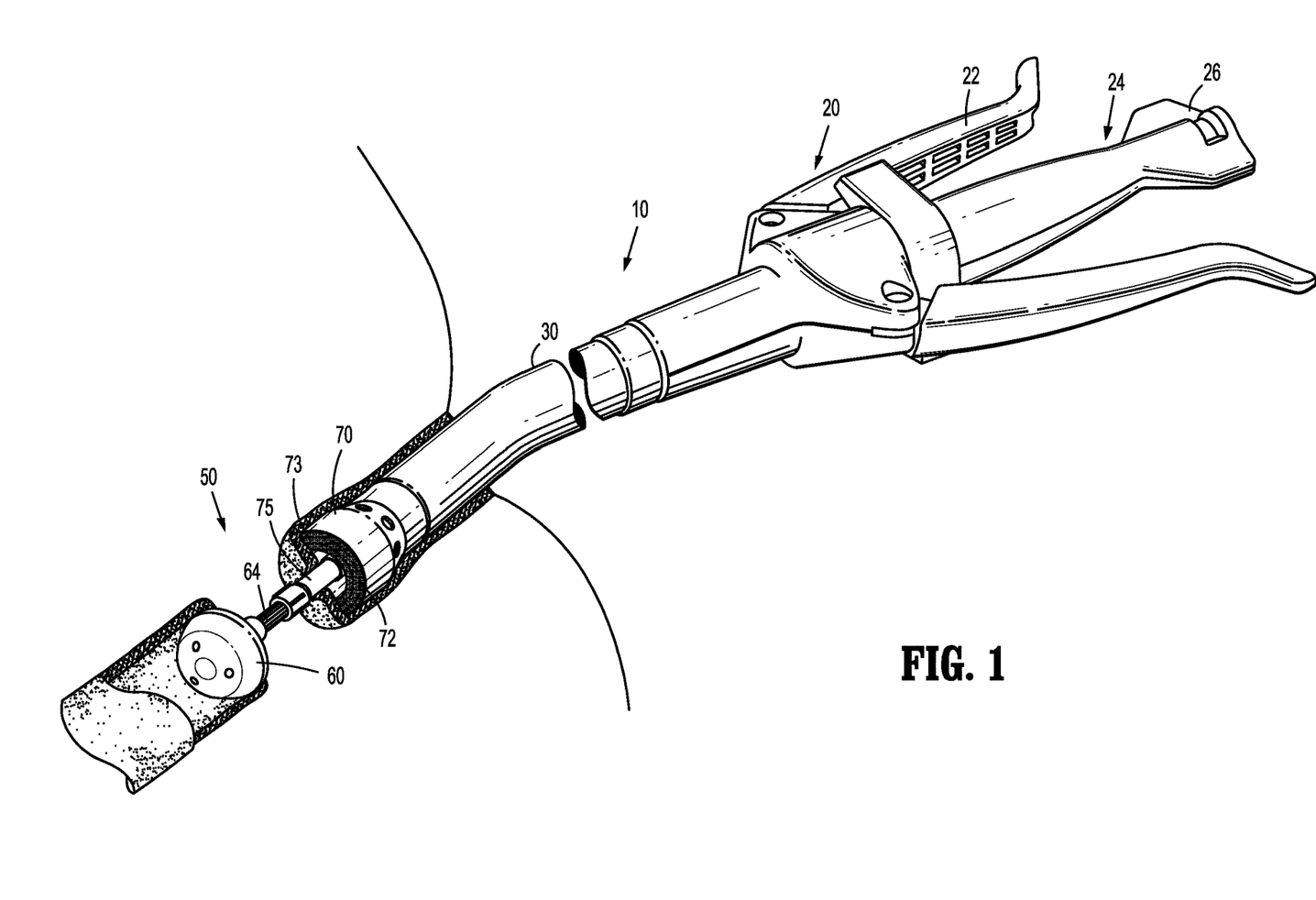
FIG. 1 is a perspective view of a surgical stapling apparatus configured for use with a surgical buttress assembly in accordance with an embodiment of the present disclosure.

With reference to FIG. 1, a surgical stapling apparatus 10 for performing circular anastomosis of hollow organs is shown. The surgical stapling apparatus 10 drives a circular array of staples (not shown) through the end sections of each organ and simultaneously fires a cylindrical knife 76 (FIG. 7) to core any tissue radially inward of the driven circular array of staples to free the tubular passage, and thereby joining two ends of the organ. The staples are of a conventional type and include a backspan having a pair of legs extending from the backspan. The legs terminate in tissue penetrating tips. The surgical stapling apparatus 10 includes a handle assembly 20 having a pair of pivotable actuating handle members 22 and an advancing means 24 including a rotatable grip member 26, an elongate body portion 30 extending distally from the handle assembly 20, and a head portion 50 including an anvil assembly 60, a staple cartridge assembly 70, and a surgical buttress assembly 100 (FIG. 2) in accordance with an embodiment of the present disclosure. The components of the surgical stapling apparatus 10 are generally formed from thermoplastics including polycarbonates, and metals including stainless steel and aluminum. The particular material selected to form a particular component may depend upon the strength requirements of the particular component.

With continued reference to FIG. 1, the handle assembly 20 can be actuated to approximate the anvil assembly 60 relative to the staple cartridge assembly 70 and to apply a plurality of annular arrays of staples through tissue. In order to properly position tissue in the head portion 50, the rotatable grip member 26 may be rotated to move the anvil assembly 60 axially relative to the staple cartridge assembly 70 between a spaced apart position and an approximated position, in which, the anvil assembly 60 is positioned adjacent the staple cartridge assembly 70 to clamp tissue therebetween. The handle members 22 may be squeezed to fire the staples through tissue to join two segments of tubular tissues together, as will be discussed in detail below.

With continued reference to FIG. 1, the elongate body portion 30 is constructed to have a slightly curved/bent shape along its length. However, the elongate body portion 30 may also be straight, as well as flexible to bend to any configuration. The length, shape and/or the diameter of the elongate body portion 30 may be tailored to suit a particular surgical procedure.

With reference to FIGS. 1-4, the head portion 50 includes the anvil assembly 60, the staple cartridge assembly 70, and the surgical buttress assembly 100 detachably secured to the anvil assembly 60. The staple cartridge assembly 70 may be fixedly connected to a distal end portion of the elongate body portion 30 or may be configured to concentrically fit within the distal end portion of the elongate body portion 30. In particular, the staple cartridge assembly 70 defines a plurality of annular arrays of staple receiving slots 72 having a staple (not shown) disposed in each one of the staple receiving slots 72.

In addition, the staple cartridge assembly 70 includes the cylindrical knife 76 (FIG. 7) concentrically arranged with the annular arrays of staples (not shown) and a plurality of staple pushers (not shown) each disposed in the respective staple receiving slot 72 to eject the respective staple through the staple receiving slot 72. The cylindrical knife 76 (FIG. 7) includes a distal rim 79 defining a knife blade adapted to cut tissue. In use, the staples travel through the staple receiving slots 72 and tissue towards the anvil assembly 60 for formation thereof. Upon actuation of the handle members 22, the cylindrical knife 76 is moved distally to cut tissue, and the plurality of pushers (not shown) are moved distally to eject the staples disposed in the staple receiving slots 72 therethrough, towards the anvil assembly 60.

Figure 2:
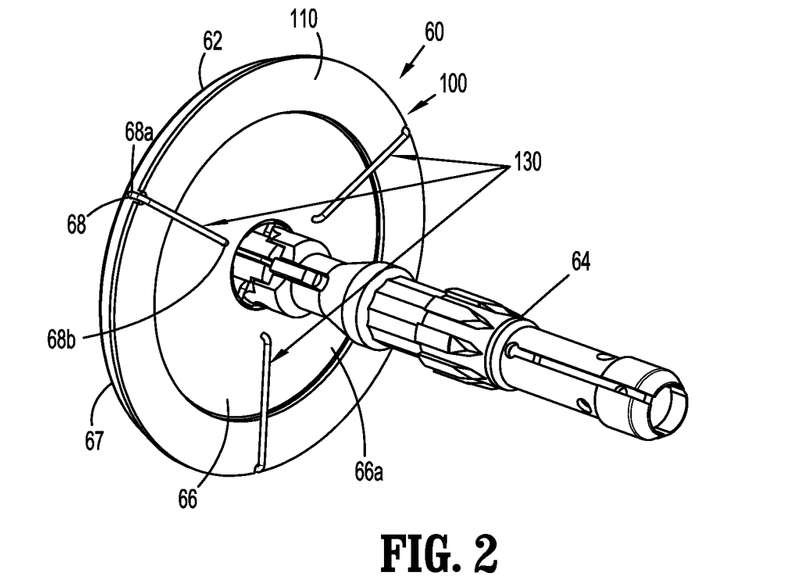
FIG. 2 is a perspective view of an anvil assembly of the surgical stapling apparatus of FIG. 1 illustrating a surgical buttress assembly mounted on the anvil assembly.

With particular reference to FIG. 2, positioned distally of the staple cartridge assembly 70 (FIG. 1) is the anvil assembly 60 including an anvil member 62 and a shaft 64 extending proximally from the anvil member 62. The anvil member 62 includes a proximal surface 66 having an outer peripheral portion (not shown). The outer peripheral portion may be, e.g., stepped, to receive the buttress member 110. The anvil member 62 defines a plurality of bores 68 dimensioned to receive a suture 130 therethrough. Each bore 68 may define a first aperture 68a in a peripheral portion 67, and a second aperture 68b defined in the inner portion 66a of the proximal surface 66. The anvil member 62 further defines a plurality of pockets (not shown) for receiving and forming the staples.

The shaft 64 is configured to detachably receive the approximation shaft 75 (FIG. 1) of the staple cartridge assembly 70. The approximation shaft 75 is operatively coupled with the rotatable grip member 26 of the handle assembly 20, whereby rotation of the rotatable grip member 26 moves the approximation shaft 75 axially. Such axial movement of the approximation shaft 75 is imparted to the anvil assembly 60 detachably coupled with the approximation shaft 75. In this manner, the anvil assembly 60 is movable axially relative to the staple cartridge assembly 70 between the spaced apart position and the approximated position, in which, the anvil assembly 60 is positioned adjacent the staple cartridge assembly 70 to adjustably clamp tissue between the anvil assembly 60 and the staple cartridge assembly 70. Examples of apparatuses for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. While manually powered apparatus are shown and described herein, it is contemplated and within the scope of the present disclosure that the apparatus include electromechanical handheld powered devices capable of performing circular anastomosis, such as, for example, the apparatus or device shown and described in U.S. Patent Publication No. US 2018-0360460, U.S. Patent Appl. Ser. No. 62/517,276, filed on Jun. 9, 2017, entitled "Handheld Electromechanical Surgical System," the entire disclosure of which is incorporated herein by reference.

Figure 3:
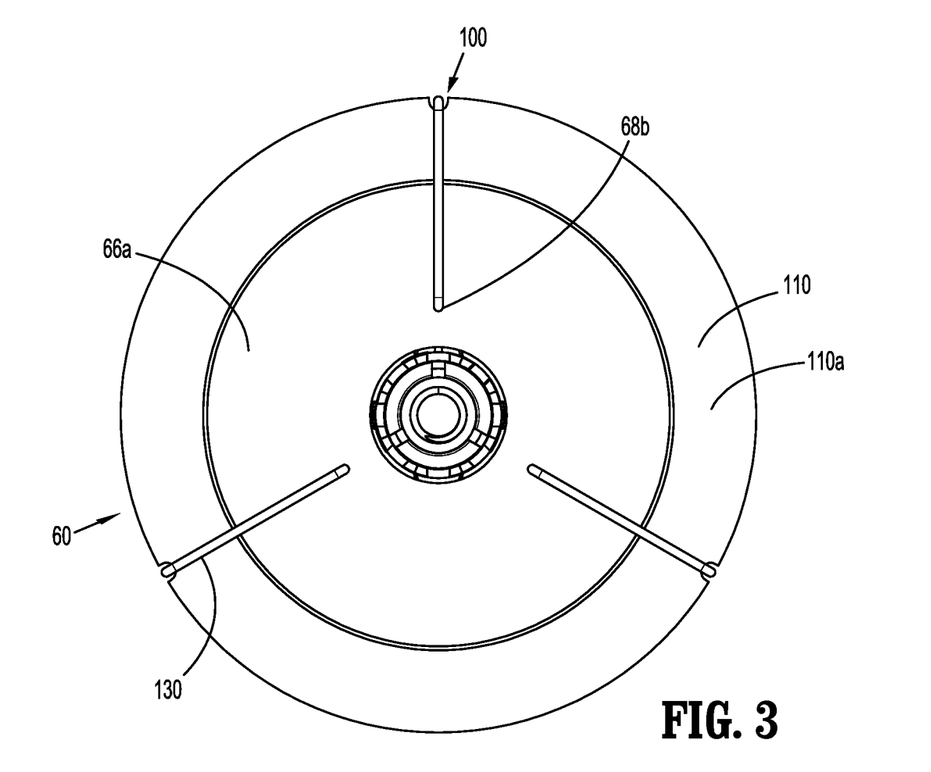
FIG. 3 is a top view of the anvil assembly of FIG. 3 having the surgical buttress assembly mounted thereon.
Figure 4:
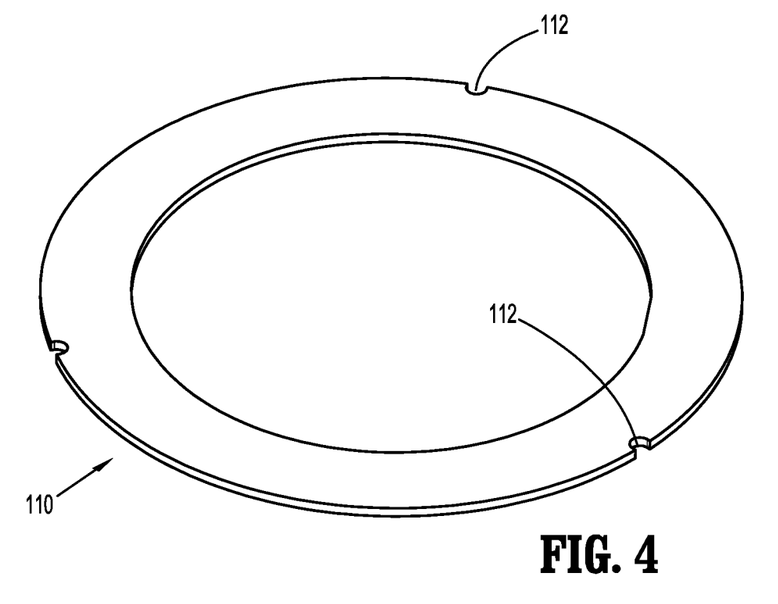

With reference now to FIGS. 2-4, the surgical buttress assembly 100 includes a buttress member 110 and a fastening member in the form of a suture 130 configured and dimensioned to secure the buttress member 110 on the anvil assembly 60. The buttress member 110 is provided to reinforce and seal staple lines applied to tissue by the surgical stapling apparatus 10. The buttress member 110 includes an annular profile configured to be concentrically aligned with the anvil assembly 60.

In use, the buttress member 110 is mounted on a proximal surface 66 of the anvil member 62. In particular, the buttress member 110 is disposed on an outer peripheral portion (not shown) of the proximal surface 66 such that the buttress member 110 is superposed with the annular arrays of the staple receiving slots 72 (FIG. 1). In this manner, when the staples are ejected through the annular arrays of the staple receiving slots 72, the legs of each staple penetrate through the buttress member 110 and the backspan of staple is secured or abuts against a proximal surface 110a of the buttress member 110. In addition, an outer peripheral portion of the proximal surface 66 of the anvil assembly 60 may be, e.g., stepped, such that the buttress member 110 mounted on the anvil assembly 60 may be flush with the inner surface 66a of the proximal surface 66. Under such a configuration, the depth of the stepped portion of the proximal surface 66 may be equivalent to a thickness of the buttress member 110.

The cylindrical knife 76 (FIG. 7) is disposed radially inward of the buttress member 110 in a superposed relation with the annular arrays of the staple receiving slots 72. In this manner, upon actuation of the handle members 22 (FIG. 1), the entire buttress member 110 is stapled to tissue to reinforce the tissue, and the need for severing of the buttress member 110 by the cylindrical knife 76 is eliminated.

With particular reference to FIGS. 2 and 4, the buttress member 110 defines a plurality of cutouts 112 circumferentially arranged around the buttress member 110. Each cutout 112 is dimensioned to receive the suture 130 therethrough to maintain the placement of the suture 130 relative to the buttress member 110. In addition, the anvil member 62 defines a plurality of bores or openings 68 dimensioned to receive the suture 130 therethrough. Each bore 68 defines the first aperture 68a in peripheral portion 67, and the second aperture 68b in the inner portion 66a of the proximal surface 66, such that the suture 130 received through the second aperture 68b extends radially outward and into the first aperture 68a via the corresponding cutout 112 of the buttress member 110. Under such a configuration, the suture 130 extending through the bore 68 may secure the buttress member 110 against the anvil member 62. Alternatively, the anvil member 62 may define discrete apertures. For example, the first and second apertures 68a, 68b may be dimensioned to receive respective first and second ends (not shown) of the suture 130, each of which, may be secured in the respective first and second aperture 68a, 68b by, e.g., friction fit or with an adhesive.

Initially, the suture 130 is looped around the buttress member 110 to secure the buttress member 110 to the anvil member 162, as described hereinabove. The surgical stapling apparatus 10 is used in an anastomosis procedure to effect joining of, for example, two opposing intestinal sections. The anastomosis procedure is typically performed using minimally invasive surgical techniques including laparoscopic means and instrumentation. Initially, a diseased intestinal section is removed. Thereafter, the anvil assembly 60 is inserted to the operative site either through a surgical incision or transanally and is positioned within a first intestinal section. The elongate body portion 30 of the surgical stapling apparatus 10, including the staple cartridge assembly 70, is inserted transanally into a second intestinal section. The first and second intestinal sections are then temporarily secured about their respective components (e.g., shaft 64 of anvil assembly 60 and the distal end of the elongate body portion 30) by conventional means such as a purse string suture (not shown).

Thereafter, the clinician maneuvers the anvil assembly 60 until the proximal end of the shaft 64 is inserted into and attached/connected to the distal end of the approximation shaft 75 of the staple cartridge assembly 10. The shaft 64 engages the approximation shaft 75 to be operable as a unitary construct. The anvil assembly 60 and the elongate body portion 30 are then approximated to approximate the first and second intestinal sections. The surgical stapling apparatus 10 is then fired causing the plurality of staple pushers (not shown) each disposed in respective staple receiving slot 72 to eject the respective staple through the slot 72. The staples travel through the first and second intestinal sections as well as the buttress member 110, towards the anvil assembly 60, thereby effecting stapling of the intestinal sections to one another, while the cylindrical knife 76 cuts a portion of tissue disposed radially inward of the cylindrical knife 76 to complete the anastomosis.

Figure 5:
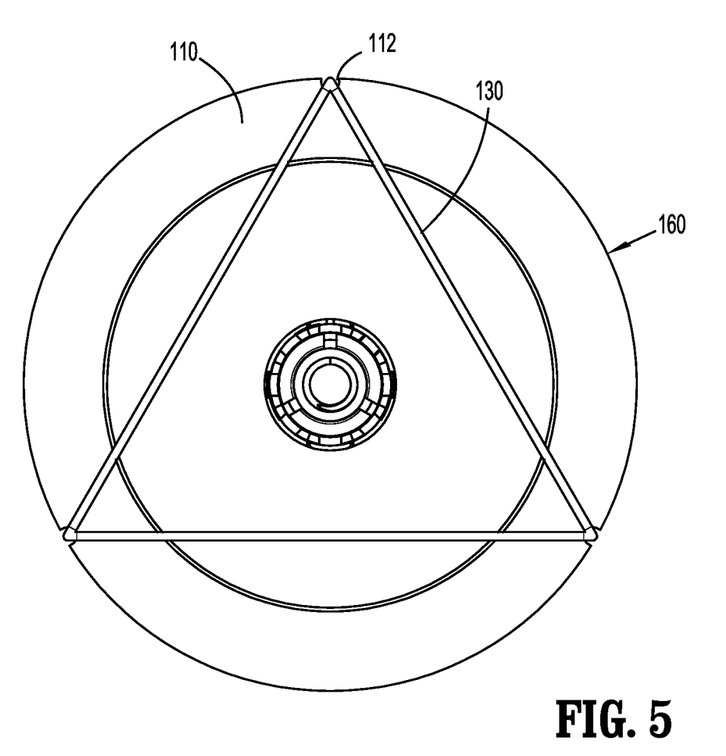
FIG. 5 is a top view of the anvil assembly of FIG. 3 having the buttress member mounted on the anvil assembly in a different configuration.
Figure 6:
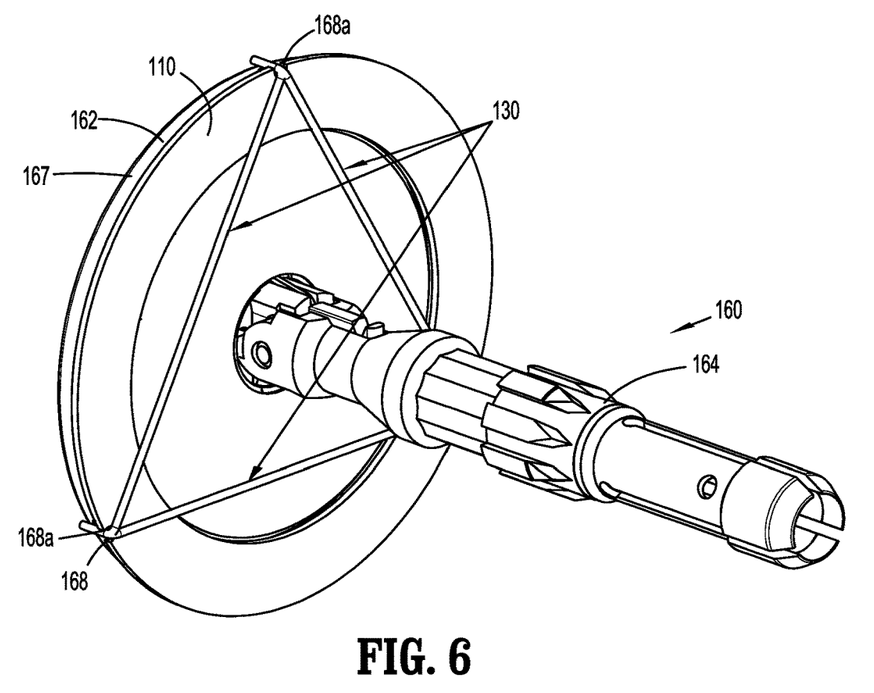
FIG. 6 is a perspective view of the anvil assembly and the surgical buttress assembly of FIG. 5.

FIGS. 5 and 6 illustrate an anvil assembly 160 in accordance with another embodiment of the present disclosure. The anvil assembly 160 is substantially identical to the anvil assembly 60 (FIG. 2) and thus identical parts in the anvil assembly 160 will not be described herein to avoid obscuring the present disclosure in unnecessary detail. The anvil assembly 160 is configured for use with the buttress member 110. In particular, the anvil assembly 160 includes an anvil member 162 and a shaft 164 extending proximally from the anvil member 162. The anvil member 162 defines a plurality of bores 168. Each bore 168 includes an aperture 168a defined in a peripheral portion 167 of the anvil member 162. The plurality of apertures 168a is, e.g., evenly, spaced apart such that when the buttress member 110 is mounted on the anvil assembly 160, the cutouts 112 of the buttress member 110 are in registration (e.g., radially) with the apertures 168a.

For example, there may be three discrete pieces of sutures 130. Each suture 130 may extend between a pair of apertures 168a to secure a portion of the buttress member 110 to the anvil assembly 160. In this manner, the sutures 130 may form, e.g., a triangular formation, across the buttress member 110. For example, the plurality of bores 168 may be in communication with each other. Alternatively, the first and second ends of each suture 130 may be secured to the respective apertures 168a by, e.g., friction fit or use of an adhesive. However, it is contemplated that a single suture may be used to have the same formation. The method of using the buttress member 110 is substantially identical to the method described hereinabove, and thus will not be described herein to avoid obscuring the present disclosure in unnecessary detail.

Figure 7:
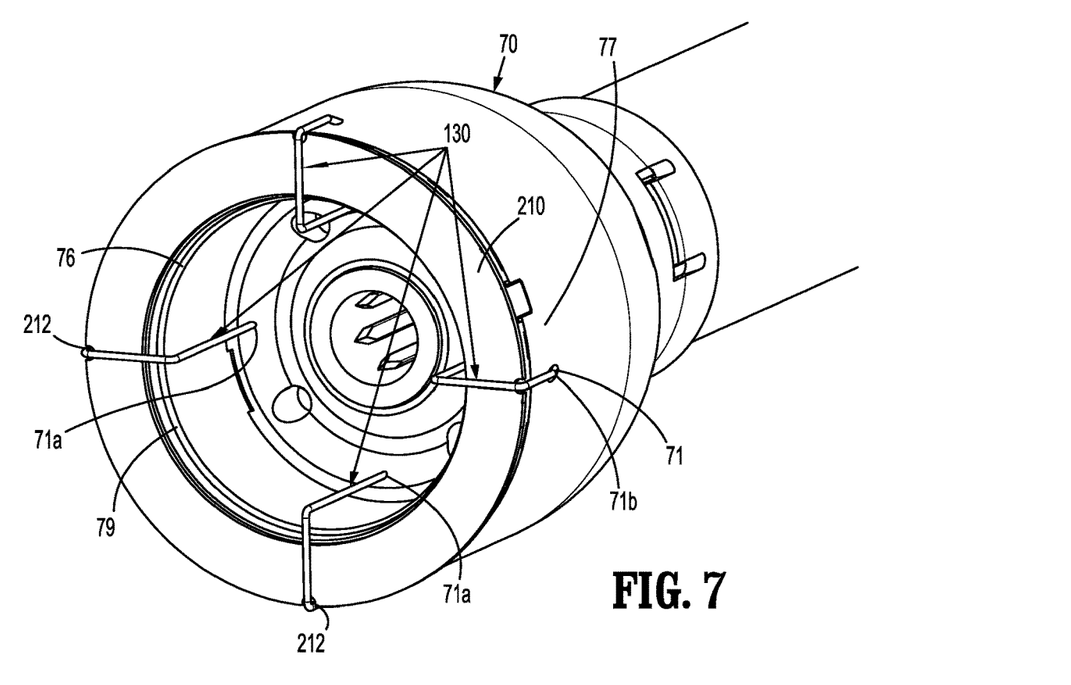
FIG. 7 is a perspective view of the staple cartridge assembly having a surgical buttress assembly in accordance with another embodiment of the present disclosure.

FIG. 7 illustrates another embodiment of a buttress member 210 that may be secured to the staple cartridge assembly 70. The buttress member 210 is substantially identical to the buttress member 110. In particular, the buttress member 210 has an additional cutout 212 compared to the buttress member 110. For example, the cutouts 212 may be evenly spaced apart such that the cutouts are, e.g., 90 degrees, apart. In particular, the buttress member 210 is mounted on a distal surface 73 (FIG. 1) defining the plurality of staple receiving slots 72. The staple cartridge assembly 70 defines a plurality of bores 71 extending through a wall 77. Each bore 71 includes inner and outer apertures 71a, 71b dimensioned to receive the suture 130 to fasten at least a portion of the buttress member 110 to the staple cartridge assembly 70. In particular, the bores 71 are evenly spaced apart and are in registration with the respective cutouts 212 of the buttress member 210. Each suture 130 extends radially outward from the inner aperture 71a to the outer aperture 71b. In this manner, each suture 130 extends through the corresponding bore 71 and secures a portion of the buttress member 110 to the staple cartridge assembly 70.

In use, when the plurality of staples are fired and the cylindrical knife 76 is moved distally, the distal rim 79 of the cylindrical knife 76 cuts the suture 130, thereby enabling separation of the buttress member 210 from the staple cartridge assembly 70. It is also contemplated that the inner and outer apertures 71a, 71b may be discrete such that first and second ends of the suture 130 are secured in the respective inner and outer apertures 71a, 71b by, e.g., friction fit or through a use of an adhesive.

Figure 8:
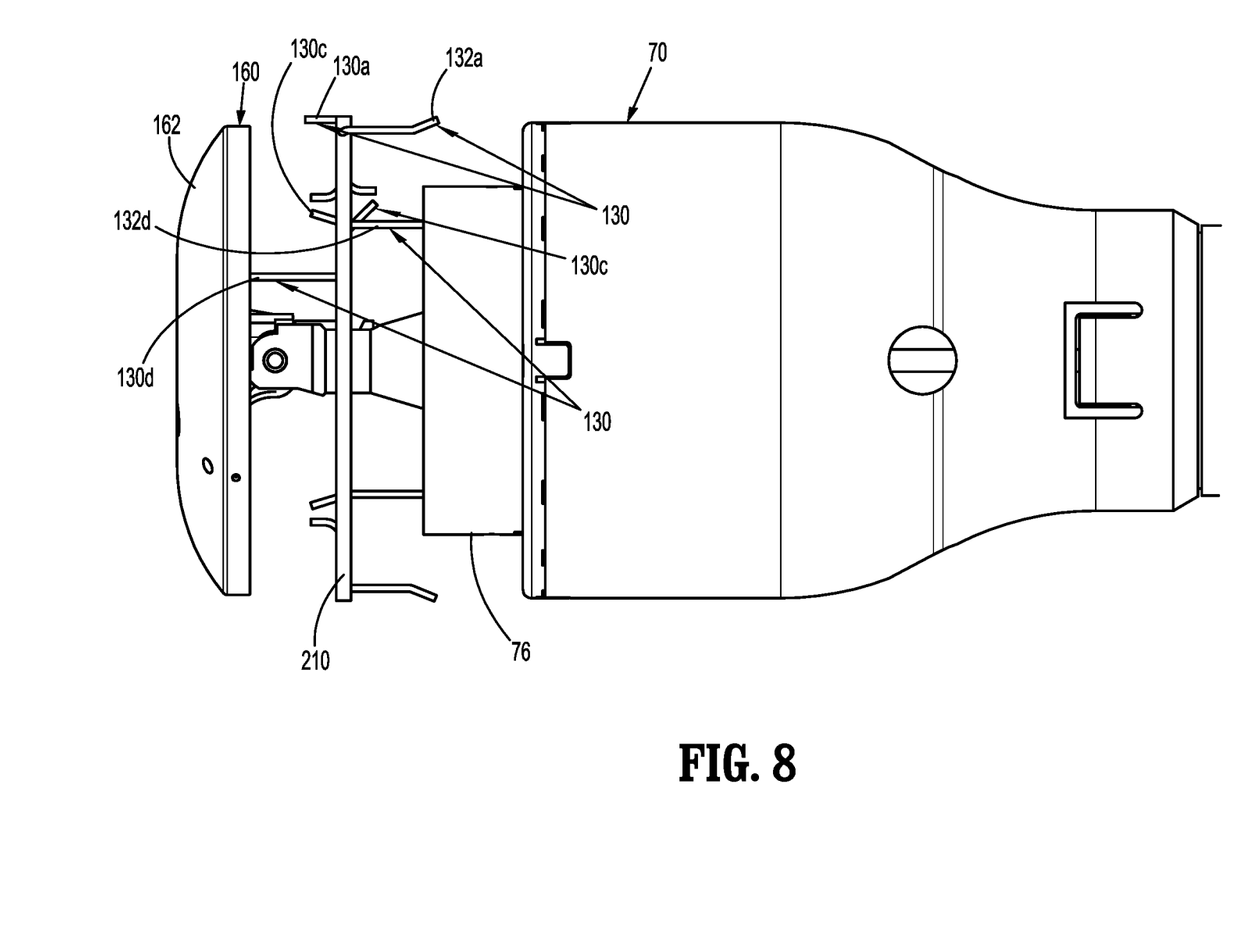
FIG. 8 is a perspective view of the staple cartridge assembly and the anvil assembly of FIG. 7 illustrating initial configuration of a surgical buttress assembly.

With reference to FIG. 8, initially, the buttress member 210 may initially be secured with the anvil assembly 60 and the staple cartridge assembly 70. For example, discrete sutures 130 may be utilized to secure the buttress member 210 to the anvil assembly 60 and the staple cartridge assembly 70. Under such a configuration, when the anvil member 62 is initially moved apart from the staple cartridge assembly 70 to the spaced apart position, ends 130a, 132a of the suture 130 are untied from the anvil member 162 and the staple cartridge assembly 70. When the staples (not shown) are fired, which, in turn, triggers the cylindrical knife 76 (FIG. 7) to move distally, the cylindrical knife 76 cuts portions 130c, 132c of the sutures 130. At this time, ends 130d, 132d of the sutures 130 remain connected to the anvil member 162 and the staple cartridge assembly 70, respectively, and are removed along with the apparatus. The method of using the buttress member 210 is substantially identical to the surgical buttress assembly 100 described hereinabove, and thus will not be described herein to avoid obscuring the present disclosure in unnecessary detail.

Figures 9, 10:
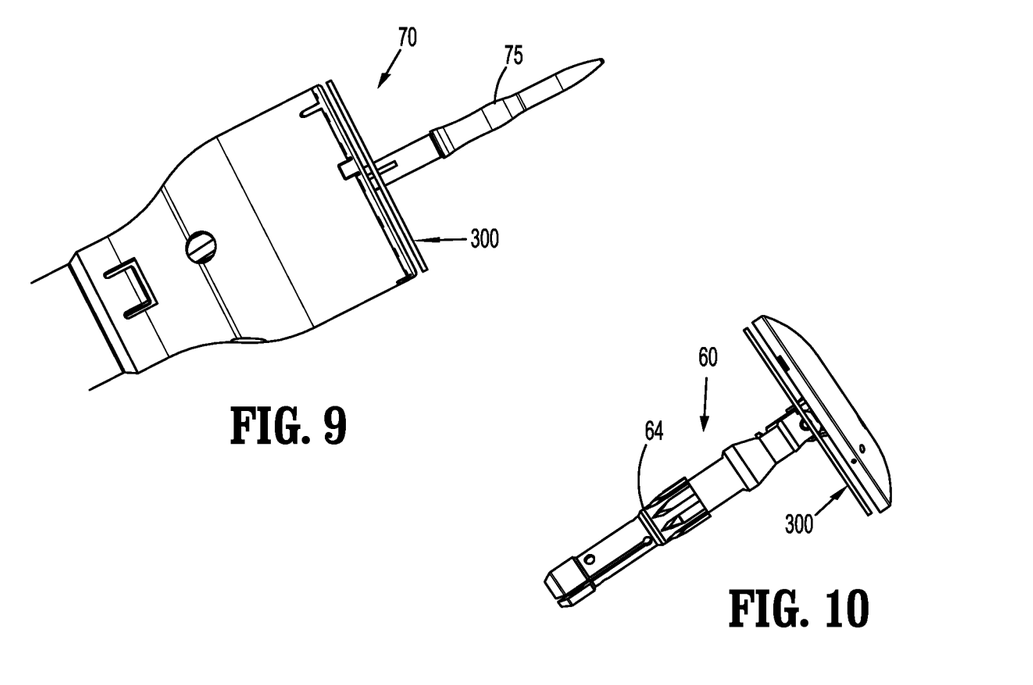
Figure 11:
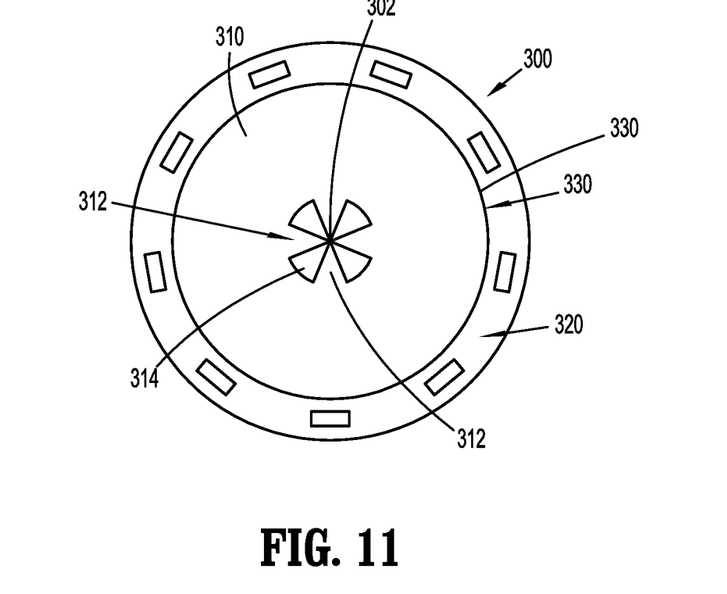
FIG. 11 is a top view of the buttress member of FIG. 10.

FIGS. 9-11 illustrate a buttress member 300 in accordance with another embodiment of the present disclosure. The buttress member 300 is configured to be secured to the anvil assembly 60 or the staple cartridge assembly 70 without use of the suture 130 (FIG. 3). In particular, the buttress member 300 includes an inner portion 310 and an outer peripheral portion 320 disposed radially outward of the inner portion 310. The inner portion 310 and the outer peripheral portion 320 are marked/separated by a boundary circle designation 330. The inner portion 310 includes a plurality of flaps 312 circumferentially arranged about the center 302 of the buttress member 300. The inner portion 310 defines a plurality of cutouts 314 also circumferentially arranged about the center 302 of the buttress member 300. Each cutout 314 is defined between a pair of flaps 312. The cutouts 314 may define a diameter substantially identical or smaller than a diameter of the approximation shaft 75 of the staple cartridge assembly 70 or the shaft 64 of the anvil assembly 60 to provide, e.g., a tight or friction fit, against the approximation shaft 75 or the shaft 64.

In particular, the flaps 312 extend radially inward and are coterminous at the center 302. It is contemplated that each flap 312 may be cantilevered or may be joined to one another at their respective tips. In addition, each flap 312 is tapered towards the center 302 of the buttress member 300. At least the inner portion 310 of the buttress member 300 may be formed of a resilient material such that the flaps 312 may resiliently flex proximally or distally, depending on a direction of the object inserted therethrough.

The outer peripheral portion 320 extends radially outward from the inner portion 310. The outer peripheral portion 320 is dimensioned to be disposed on the outer peripheral portion (not shown) of the proximal surface 66 (FIG. 2) of the anvil assembly 60 such that the buttress member 300 is superposed with the plurality of annular arrays of the staple receiving slots 72 (FIG. 1). In this manner, when the staples are ejected through the plurality of annular arrays of the staple receiving slots 72, the legs of each staple penetrate through the buttress member 300 and the backspan of staple is secured or abuts against a proximal surface of the buttress member 300. In addition, the outer peripheral portion 320 is dimensioned to be disposed on the distal surface 73 (FIG. 1) of the staple cartridge assembly 70. The cylindrical knife 76 (FIG. 7) is disposed radially inward of the outer peripheral portion 320. Under such a configuration, the buttress member 300 may be secured with the anvil assembly 60 or the staple cartridge assembly 70 without having to use the suture 130. Furthermore, the inner portion 310 of the buttress member 300 that is utilized to secure the buttress member 300 to the anvil assembly 60 or the staple cartridge assembly 70 is severed from the outer peripheral portion 320 that is stapled to tissue, by the cylindrical knife 76. The boundary circle designation 330 indicates the area radially inward of the outer peripheral portion 320 that will be severed from the outer peripheral portion 320. The method of using the buttress member 300 is substantially identical to the surgical buttress assembly 100 described hereinabove, and thus will not be described herein to avoid obscuring the present disclosure in unnecessary detail.

Figure 12:
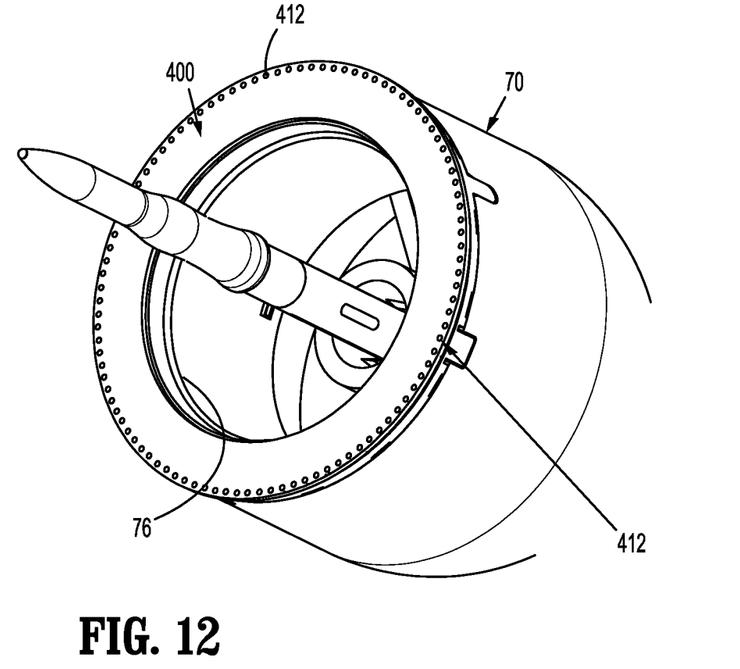
FIG. 12 is a perspective view of the staple cartridge assembly of FIG. 1 having a buttress member in accordance with another embodiment of the present disclosure.
Figure 13:
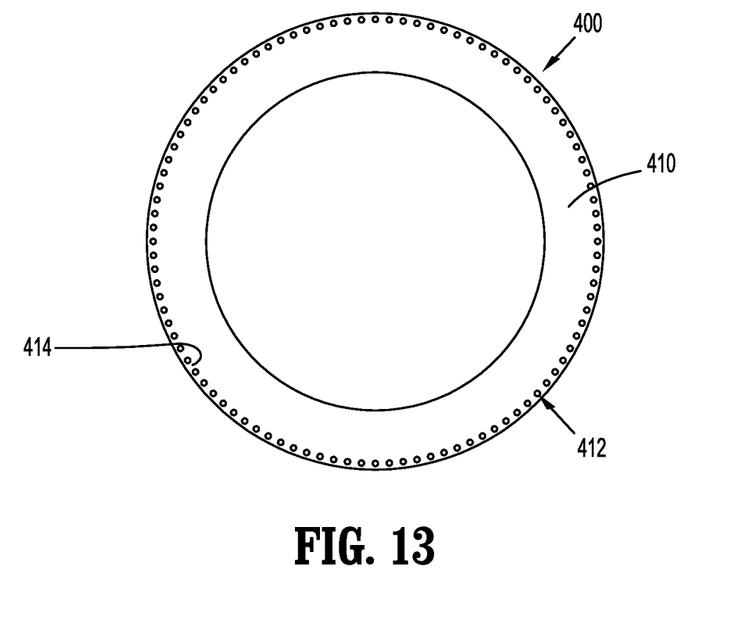
FIG. 13 is a top view of the buttress member of FIG. 12.

FIGS. 12 and 13 show a buttress member 400 in accordance with another embodiment of the present disclosure. The buttress member 400 includes an annular member 410. The annular member 410 is configured and dimensioned to be flush with an outer peripheral edge of anvil member 62 (FIG. 2) when mounted on the anvil member 62. The annular member 410 is dimensioned to be disposed on the distal surface 73 (FIG. 1) of the staple cartridge assembly 70 and is secured to the distal surface 73 by the use of an adhesive or a gel such as, e.g., hydrogel, such that the buttress member 400 is superposed with the plurality of annular arrays of the staple receiving slots 72. In this manner, when the staples are ejected through the plurality of annular arrays of the staple receiving slots 72, the legs of each staple penetrate through buttress member 400 and the backspan of staple is secured or abuts against a proximal surface of buttress member 400.

The annular member 410 defines a plurality of perforations 412 to receive an adhesive or a gel such as, e.g., hydrogel, therein. The plurality of the perforations 412 may be defined at a peripheral portion 414 or the radially outermost portion of the annular member 410. The plurality of perforations defined in the peripheral portion 414 of the annular member 410 enables deposit of the adhesive and improves securement of the buttress member 400 to the target surface, such as, e.g., the distal surface 73 (FIG. 1) of the staple cartridge assembly 70. The surgical buttress member 400 is positioned radially outward of the cylindrical knife 76 (FIG. 7). As such, upon actuation of the handle members 22 (FIG. 1), the entire buttress member 112 is stapled to tissue to reinforce the tissue, and severing of the buttress member 400 by the cylindrical knife 76 is eliminated.

It is also contemplated that the buttress member 400 may be configured to be mounted on the outer peripheral portion (not shown) of the proximal surface 66 of the anvil assembly 60 by the use of the adhesive. The use and operation of the buttress member 400 is substantially similar to the use and operation of the surgical buttress assembly 100 described hereinabove, and thus will not be described further herein.

Each of the buttress members 110, 210, 300, 400 may be monolithically formed as a single construct. The buttress members 110, 210, 300, 400 may be fabricated from a biocompatible material which is bio-absorbable or non-absorbable, as well as natural or synthetic materials. It should be understood that any combination of natural, synthetic, bio-absorbable, and non-bioabsorbable materials may be used to form the buttress members 110, 210, 300, 400. In addition, the buttress members 110, 210, 300, 400 may be porous, non-porous, or combinations thereof. It is also envisioned that the buttress members 110, 210, 300, 400 described herein may contain a plurality of layers in which any combination of non-porous and porous layers may be configured. For example, the buttress members 110, 210, 300, 400 may be formed to include multiple non-porous layers and porous layers that are stacked in an alternating manner. In another example, the buttress members 110, 210, 300, 400 may be formed in a "sandwich-like" manner wherein the outer layers of buttress members 110, 210, 300, 400 may include porous layers and the inner layers are non-porous layers. Examples of multi-layered buttress members are disclosed in U.S. Patent Application Publication No. 2009/0001122, filed on Jun. 27, 2007, entitled "Buttress and Surgical Stapling Apparatus," the entire disclosure of which is incorporated by reference therein.

In particular, the use of non-porous layers in the buttress members 110, 210, 300, 400 may enhance the ability of the buttress members 110, 210, 300, 400 to resist tears and perforations during the manufacturing, shipping, handling, and stapling processes. In addition, the use of a non-porous layer in the surgical buttress may also retard or inhibit tissue ingrowth from surrounding tissues, and thereby acting as an adhesion barrier and inhibiting the formation of unwanted scar tissue.

In addition, at least one bioactive agent may be combined with the buttress members 110, 210, 300, 400. The agent may be disposed on a surface of the surgical buttress and/or impregnated therein. In these embodiments, the buttress members 110, 210, 300, 400 can also serve as a vehicle for delivery of the bioactive agent. The term "bioactive agent,"

as used herein, is used in its broadest sense and includes any substance or mixture of substances that have clinical use.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. An apparatus for joining two hollow organ sections with an annular array of surgical staples, the apparatus comprising:
    a staple cartridge assembly including an annular wall having the annular array of surgical staples, the annular wall defining an inner aperture in an inner surface of the annular wall and an outer aperture in an outer surface of the annular wall, the inner aperture and the outer aperture being in communication with each other to define a bore therebetween;
    an anvil assembly movable relative to the staple cartridge assembly between spaced apart and approximated positions to adjustably clamp the two hollow organ sections between the staple cartridge and anvil assemblies;
    a buttress member configured to be positioned on a distal surface of the staple cartridge assembly, the buttress member defining a cutout on a peripheral portion thereof; and
    a fastening member having a first end securely affixed to the inner aperture of the annular wall of the staple cartridge assembly and a second end securely affixed to the outer aperture of the annular wall of the staple cartridge assembly to secure the buttress member on the staple cartridge assembly, wherein the cutout of the buttress member is in radial registration with the outer aperture of the annular wall.

2. The apparatus according to claim 1, wherein the cutout of the buttress member is dimensioned to receive the fastening member therethrough.

3. The apparatus according to claim 1, wherein at least one of the first end or the second end of the fastening member is securely affixed to the respective inner or outer apertures by an adhesive.

4. The apparatus according to claim 1, wherein the fastening member is dimensioned to be received through the bore of the annular wall of the staple cartridge assembly such that the first and second ends extending through the first and second apertures are tied to secure the buttress member on the staple cartridge assembly.

5. The apparatus according to claim 1, wherein the buttress member has an annular configuration, the buttress member concentrically disposed in a juxtaposed relation with the annular array of surgical staples.

6. The apparatus according to claim 1, wherein the buttress member further defines a plurality of cutouts circumferentially arranged around the peripheral portion of the buttress member.

7. The apparatus according to claim 1, wherein the staple cartridge assembly further includes a cylindrical knife disposed radially inward of the buttress member.

8. The apparatus according to claim 7, wherein the fastening member secured to the inner and outer apertures of the annular wall of the staple cartridge assembly is looped around the cylindrical knife such that the fastening member is severed by the cylindrical knife when the cylindrical knife is axially displaced.

9. The apparatus according to claim 1, wherein the fastening member is a suture.

10. An apparatus for joining two hollow organ sections with an annular array of surgical staples, the apparatus comprising:
    a staple cartridge assembly including the annular array of surgical staples;
    an anvil assembly movable relative to the staple cartridge assembly between spaced apart and approximated positions to adjustably clamp the two hollow organ sections between the staple cartridge and anvil assemblies, the anvil assembly including an anvil member and a shaft extending from the anvil member, the anvil member including a proximal surface defining a first aperture and a peripheral portion defining a second aperture; and
    a buttress assembly including a buttress member and a fastening member, the buttress member dimensioned to be positioned on the proximal surface of the anvil assembly, the buttress member secured to the anvil assembly by the fastening member having a first end affixed to the first aperture and a second end affixed to the second aperture, wherein the buttress member defines a cutout dimensioned to receive the fastening member therethrough.

11. The apparatus according to claim 10, wherein the cutout of the buttress member is in registration with the second aperture of the anvil member.

12. The apparatus according to claim 10, wherein the first and second apertures of the anvil assembly are in communication with each other to define a bore dimensioned to receive the fastening member therethrough.

13. The apparatus according to claim 10, wherein an outer peripheral portion of the proximal surface of the anvil member includes a stepped portion configured to receive the buttress member such that the buttress member is flush with an inner member of the proximal surface of the anvil member, the inner member radially inward of the outer peripheral portion of the proximal surface.

14. The apparatus according to claim 10, further comprising a cylindrical knife concentrically arranged in the staple cartridge assembly and with the buttress member, the knife member movable relative to the staple cartridge assembly.

15. The apparatus according to claim 14, wherein the buttress member is configured to be disposed radially outward of the knife member.

16. An apparatus for joining two hollow organ sections with an annular array of surgical staples, the apparatus comprising:
    a staple cartridge assembly including:
        an annular wall having the annular array of surgical staples, the annular wall defining an inner aperture in an inner surface of the annular wall and an outer aperture in an outer surface of the annular wall; and
        a cylindrical knife disposed radially inward of the buttress member;
    an anvil assembly movable relative to the staple cartridge assembly between spaced apart and approximated positions to adjustably clamp the two hollow organ sections between the staple cartridge and anvil assemblies;
    a buttress member configured to be positioned on a distal surface of the staple cartridge assembly, the buttress member defining a cutout on a peripheral portion thereof, the cutout being in radial registration with the outer aperture of the annular wall; and a fastening member having a first end securely affixed to the inner aperture of the annular wall of the staple cartridge assembly and a second end securely affixed to the outer aperture of the annular wall of the staple cartridge assembly to secure the buttress member on the staple cartridge assembly, wherein the fastening member secured to the inner and outer apertures of the annular wall of the staple cartridge assembly is looped around the cylindrical knife such that the fastening member is severed by the cylindrical knife when the cylindrical knife is axially displaced.

17. The apparatus according to claim 16, wherein the inner aperture and the outer aperture are in communication with each other to define a bore therebetween.

* * * * *